US008486272B2

(12) United States Patent
Rauch

(10) Patent No.: US 8,486,272 B2
(45) Date of Patent: Jul. 16, 2013

(54) METHOD AND DEVICE FOR MAINTAINING A CONSTANT PH VALUE OF A MEDICAL LIQUID DURING THE DISPENSING THEREOF FROM A CONTAINER

(75) Inventor: Achim Rauch, Langweiler (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 628 days.

(21) Appl. No.: 12/733,116

(22) PCT Filed: Jul. 31, 2008

(86) PCT No.: PCT/EP2008/006328
§ 371 (c)(1),
(2), (4) Date: Feb. 12, 2010

(87) PCT Pub. No.: WO2009/018961
PCT Pub. Date: Feb. 12, 2009

(65) Prior Publication Data
US 2010/0140184 A1 Jun. 10, 2010

(30) Foreign Application Priority Data
Aug. 7, 2007 (DE) .......................... 10 2007 037 099

(51) Int. Cl.
*B01F 3/04* (2006.01)
*A61K 33/10* (2006.01)
(52) U.S. Cl.
USPC ................................ 210/744; 210/743; 221/1

(58) Field of Classification Search
USPC ................................................ 210/743, 744
See application file for complete search history.

(56) References Cited

U.S. PATENT DOCUMENTS

| 3,878,664 A | * | 4/1975 | Zinke ............................. 53/432 |
| 2008/0017588 A1 | | 1/2008 | Okazaki et al. |

FOREIGN PATENT DOCUMENTS

| DE | 2 358 759 A1 | 6/1974 |
| EP | 0 481 257 | 4/1992 |
| EP | 0 491 981 B1 | 7/1992 |
| WO | WO 03/086973 A1 | 10/2003 |
| WO | WO 2006/090869 A1 | 8/2006 |

OTHER PUBLICATIONS

Machine Translation of EP0491981A1.*

\* cited by examiner

*Primary Examiner* — Duane Smith
*Assistant Examiner* — Paul J Durand
(74) *Attorney, Agent, or Firm* — Jacobson Holman PLLC

(57) ABSTRACT

A method for keeping constant a pH of a medical liquid being drained from a container includes adding $CO_2$ and at least one other gas or gas mixture to the container during the draining of the medical liquid. An apparatus associated with the method has an outflow for the medical liquid, at least one inflow for the $CO_2$ and an inflow for the other gas or gas mixture, and an electronic control for the determination and automatic supply of a quantity of the $CO_2$ during the draining of the medical liquid.

14 Claims, 3 Drawing Sheets

METHOD AND DEVICE FOR MAINTAINING A CONSTANT PH VALUE OF A MEDICAL LIQUID DURING THE DISPENSING THEREOF FROM A CONTAINER

CROSS-REFERENCE TO RELATED APPLICATION

This is a national stage of PCT/EP08/006,328 filed Jul. 31, 2008 and published in German, which has a priority of German no. 10 2007 037 099.9 filed Aug. 7, 2007, hereby incorporated by reference.

BACKGROUND OF THE INVENTION

1. Field of Invention

The present invention relates to a method and to an apparatus for the keeping constant of a pH of a medical liquid when draining from a container. Such a method and such an apparatus are in particular used in the manufacture and filling of medical liquids, in particular in the manufacture and filling of medical solutions such as a bicarbonate dialysis solution.

2. Description of the Prior Art

Such medical liquids are manufactured in so-called batch containers under sterile conditions from water (WFI—water for injection) and the soluble additives. The batch containers have e.g. a size of around 24,000 liters and are filled with liquid with a changing level. A gas space is located above the liquid level in the container and is in a complex interaction with the solution with respect to the chemical-physical equilibrium. The medical liquid, e.g. a bicarbonate solution, should always have a defined pH within very narrow tolerances. A stripping of $CO_2$ from the solution into the gas space occurs as a disturbance variable in this connection, which results in an increase in pH.

To counter this, in known methods, the solution is gassed with $CO_2$, with the $CO_2$ being injected into the solution via nozzles in the region of the base of the batch container (reactor). The fact that pH sensors drift or show measured value differences as time passes and therefore have to be calibrated regularly in particular has an aggravating effect. However, in the case of inline sensors, this contradicts the maintenance of the sterile conditions. In this connection, an increase in the pH due to the gassing of $CO_2$ is countered such that deviations from the desired value are determined on the basis of solution samples to be taken manually at regular intervals with a subsequent laboratory determination of the pH and thereupon the solution is gassed with $CO_2$ in accordance with values based on experience via nozzles at the reactor base. A typical 2-point controller development of the pH thereby results over the manufacturing period. The control deviation of the pH is considerable due to the huge time requirement of analytical chemistry. The manufacturing method is correspondingly sluggish. In addition, this method of maintaining a constant pH is extremely personnel-intensive and eludes automation. The fact that pH sensors drift or show measured value differences as time passes and therefore have to be calibrated regularly in particular has an aggravating effect. However, in the case of inline sensors, this contradicts the maintenance of the sterile conditions.

SUMMARY OF THE INVENTION

It is therefore the object of the present invention to provide a method and an apparatus for the keeping constant of a pH of a medical liquid when draining from a container which is simpler, more time-saving and more cost-effective. It is equally the object of the present invention to make possible an automation of the method of maintaining a constant pH of a medical liquid when draining from a container.

This object is solved in accordance with the invention by a method of keeping constant a pH of a medical liquid when draining from a container as described herein. In this method, in accordance with the invention, $CO_2$ and at least one further gas or gas mixture flows into the container during the draining of the medical liquid. The present invention makes use of the recognition that liquid and gas space in the container interact closely with one another. In this process, $CO_2$ is gassed from the liquid at a partial $CO_2$ pressure below the equilibrium conditions for so long while increasing the pH until the liquid and the gas space above it are in chemical-physical equilibrium. Vice versa, with a partial $CO_2$ pressure above the equilibrium conditions in the gas space, $CO_2$ is absorbed by the liquid, which results in a pH reduction. In this connection, the portion of $CO_2$ in the gas space atmosphere is decisive for the physical-chemical equilibrium with respect to the pH of the liquid while taking account of the physical-chemical marginal conditions such as the pressure and the temperature in the gas space and in the solution. On a draining of the liquid by the lowering of the liquid level and the accompanying increase in size of the gas space above the medical liquid, the physical marginal conditions of the chemical-physical equilibrium between the liquid and the gas space change which, in the known method described above, results in the pH shift which then subsequently has to be corrected. It is now possible, in contrast, due to the inflow of $CO_2$ and at least one further gas or gas mixture in accordance with the present invention, to maintain the originally set chemical-physical equilibrium or the reached chemical-physical equilibrium by a corresponding supply of $CO_2$ and of at least one further gas or gas mixture despite the varying physical marginal conditions of the gas space on the draining of the liquid so that a shift in the pH does not occur at all. The inflow of the at least one further gas or gas mixture in addition to $CO_2$ is decisive to be able to satisfy the equilibrium conditions. The further gas or gas mixture should advantageously not appreciably react with the liquid at least with respect to the $CO_2$ and/or should only contain small or negligible quantities of $CO_2$. In particular air can be used as the further gas mixture in this connection.

The method in accordance with the invention has the advantage that the pH can be kept constant in a simple manner, with fluctuations already being prevented right from the start instead of compensating them later. A maintenance of the pH thus results with a simpler and faster method procedure, which can moreover be automated.

The method in accordance with the invention has the further advantage that the method for the observation of the desired pH via corresponding taking of solution samples with a subsequent laboratory determination of the pH, which are anyway unsatisfactory, can be replaced by a simple method in which no chemical pH analysis is required at all. A pH determination is in particular only necessary once after completing the manufacturing and filling procedure for the final quality control of the solution required by law.

In the method in accordance with the invention, a quantity of $CO_2$ to be added is advantageously determined and added in a controlled manner based on the determination. The quantity of $CO_2$ which is necessary on the draining of the liquid to maintain the pH in the liquid can in particular thus be calculated and added in a controlled manner. In this connection, the pH of the solution can be kept constant by the maintenance of the chemical-physical equilibrium between the liquid and the gas space by the controlled supply of $CO_2$ based on the calculation. The required $CO_2$ quantity must in particular be determined which is required for the maintenance of the chemical-physical equilibrium with respect to the likewise inflowing at least one further gas or gas mixture.

In the method in accordance with the invention, a change in the filling level of the liquid is advantageously measured and the quantity of $CO_2$ added into the container is determined based on the measurement. The change in the filling level can be measured e.g. in a contact-less manner via a radar sensor. The change in the filling level as a control variable for the addition of $CO_2$ permits a simple and nevertheless effective control of the $CO_2$ supply.

Further advantageously, in the method in accordance with the invention, a change in the gas space volume in the container above the liquid is determined, in particular based on the above-described change in the filling level of the liquid, with the amount of $CO_2$ to be added being determined in dependence on this change in the gas space volume. It can hereby be taken into account that the physical marginal conditions of the gas space vary due to the change in the gas space volume so that a corresponding $CO_2$ quantity has to be added to maintain the chemical-physical equilibrium between the gas space and the liquid.

Further advantageously, in the method in accordance with the invention, ambient air flows behind over a sterile filter so that, on a change in the filling level of the liquid, the pressure in the gas space is automatically approximated to the ambient pressure. The ambient air thus represents the at least one gas mixture which flows into the container together with the $CO_2$ when medical liquid is drained from the container. An automatic pressure compensation is thus provided by the subsequent flowing over the sterile filter without any complicated feedback control or control being necessary here so that the maintenance of the physical-chemical equilibrium is simplified. The sterile filter is absolutely necessary in this context to prevent contamination of the liquid. A particularly simple procedure in particular results in combination with a controlled addition of $CO_2$ which equalizes the inflow of external air with a low $CO_2$ content over the sterile filter and thus maintains the physical-chemical equilibrium.

Further advantageously, in the method in accordance with the invention, the $CO_2$ is added in such a quantity that a mean $CO_2$ volume portion in the gas space determined by calculation remains constant in the gas space. Investigations of the inventor have shown that such an addition of $CO_2$ based on a mean $CO_2$ volume portion determined by calculation is exceptionally suited to keep the pH of the liquid constant over the whole drainage process. A measurement of the $CO_2$ volume portion would, in contrast, hardly be possible or sensible since the partial $CO_2$ pressure or the $CO_2$ volume portion only represents a theoretical value which cannot, however, be measured sensibly in the gas space of a mixed gas because a separation and a concentration gradient formation occurs in the gas space in practice due to the different gas densities. Accordingly, the theoretical partial $CO_2$ pressure required to observe the chemical-physical equilibrium could hardly be meaningfully checked. By the addition of $CO_2$ based on the mean $CO_2$ volume portion in the gas space determined by calculation, such a measurement of the partial $CO_2$ pressure, in contrast, becomes superfluous in the present invention. The investigations of the inventors have rather shown that the pH of the liquid can be kept constant in that the increase in size of the gas space is taken into account by a corresponding addition of $CO_2$.

Further advantageously, in the method in accordance with the invention, the amount of $CO_2$ to be added is determined on the basis of a chemical-physical equilibrium between the liquid and the gas space disposed above it determined by calculation. In this connection, in particular the required $CO_2$ volume portion of the gas space can be determined in advance based on the desired pH of the liquid and on further marginal conditions such as the temperature and the pressure with reference to a chemical-physical equilibrium determined by calculation. Said volume portion can then be kept constant in accordance with the invention in order also to keep the pH in the liquid constant. Investigations of the inventor have shown that this mean $CO_2$ volume portion of the chemical-physical equilibrium state determined by calculation cannot be measured locally due to the different gas densities of the gases and the gradient formation of the gas concentration associated therewith in the gas space. Nevertheless, on the addition of a quantity of $CO_2$ which results by calculation in the determined mean $CO_2$ volume portion of the equilibrium state, the pH in the solution is kept constant. The determination and/or examination of the amount of $CO_2$ to be added in accordance with the invention is likewise possible by measurement series whose results can then be stored in a memory.

The determination of the amount of $CO_2$ to be added advantageously takes place without a measurement of the pH of the liquid being carried out during the draining. Such measurements are time-consuming and make the method expensive. Such a measurement can be dispensed with in accordance with the invention as described above.

The determination of the amount of $CO_2$ to be added advantageously takes place without a measurement of the $CO_2$ concentration in the gas space. As already described above, such a measurement is anyway hardly possible and can hardly be carried out meaningfully. In accordance with the invention, as described above, such a method can be dispensed with, in particular in that $CO_2$ is added in such a quantity that a mean $CO_2$ volume portion determined by calculation remains constant in the gas space.

In this connection, the $CO_2$ and the at least one further gas or gas mixture advantageously flows above the liquid level into the gas space during the filling in the method in accordance with the invention. The $CO_2$ and the at least one further gas or gas mixture thus flows directly into the gas space to keep the gas space atmosphere in chemical-physical equilibrium with the liquid.

Further advantageously, however, a previously determined quantity of $CO_2$ is injected into the liquid by nozzle before the draining of the liquid. In this connection, in accordance with the invention, a quantity of $CO_2$ previously determined on the basis of chemical-physical calculations is initially injected into the solution by nozzle after the end of the preparation process of filling in water and adding the soluble additives, during which no measures at all are taken to set a specific pH, but rather the stripping of any $CO_2$ already present is accepted. Injector nozzles are advantageously used in this connection which permit the fine-beaded injection by nozzle at a high pulse exchange between the gas phase and the liquid phase. A specific pH hereby initially results in the solution, with a physical-chemical equilibrium being adopted between the liquid and the gas space disposed thereabove. An outflow of gas from the gas space during the injection by nozzle can advantageously be suppressed for this purpose. This chemical-physical equilibrium is then maintained in accordance with the invention according to the method such as was described above in order thus also to maintain the pH.

The method in accordance with the invention is advantageously used in the manufacture or draining of a bicarbonate solution. The above-described problem of the stripping of $CO_2$ from the solution in particular occurs with such a bicarbonate solution so that here, in accordance with the invention, the pH can be kept constant via the maintenance of the physical-chemical equilibrium.

The present invention furthermore includes an apparatus for the keeping constant of a pH of a medical liquid when draining from a container, with the container having an outlet for the liquid, at least one inlet for $CO_2$ as well as an inlet for at least one further gas or gas mixture. In accordance with the invention, the apparatus has an electronic control for the determination and automatic supply of a $CO_2$ quantity for the initial solution setting by means of the gas/liquid nozzles and/or during the draining of the liquid. The determination and automatic supply of the $CO_2$ quantity in particular takes place in accordance with one of the methods in accordance with the invention described above. The same advantages hereby result such as were described above with respect to the method. The container advantageously has a respective inlet for $CO_2$ into the liquid and for $CO_2$ into the gas space.

Further advantageously, the apparatus in accordance with the invention has a transducer for the determination of the filling level in the container, in particular via microwaves (radar). The filling level in the container can be determined via this transducer so that the $CO_2$ amount to be supplied can be controlled via the filling level and/or the reduction in the filling level.

Further advantageously, the apparatus in accordance with the invention has a connection between the gas space of the container and the environment through which ambient air can flow into the gas space via a sterile filter. This connection thus represents the inflow for the at least one further gas or gas mixture and provides an automatic pressure compensation as well as an inflow of ambient air. The physical-chemical equilibrium is maintained by a simultaneous supply of $CO_2$ via the electronic control.

Further advantageously, the invention includes an apparatus for the carrying out of a method such as was described above.

BRIEF DESCRIPTION OF THE DRAWINGS

The present invention will now be represented in more detail with reference to drawings and to an embodiment. There are shown.

DETAILED DESCRIPTION OF THE PREFERRED EMBODIMENTS

Figure 1:
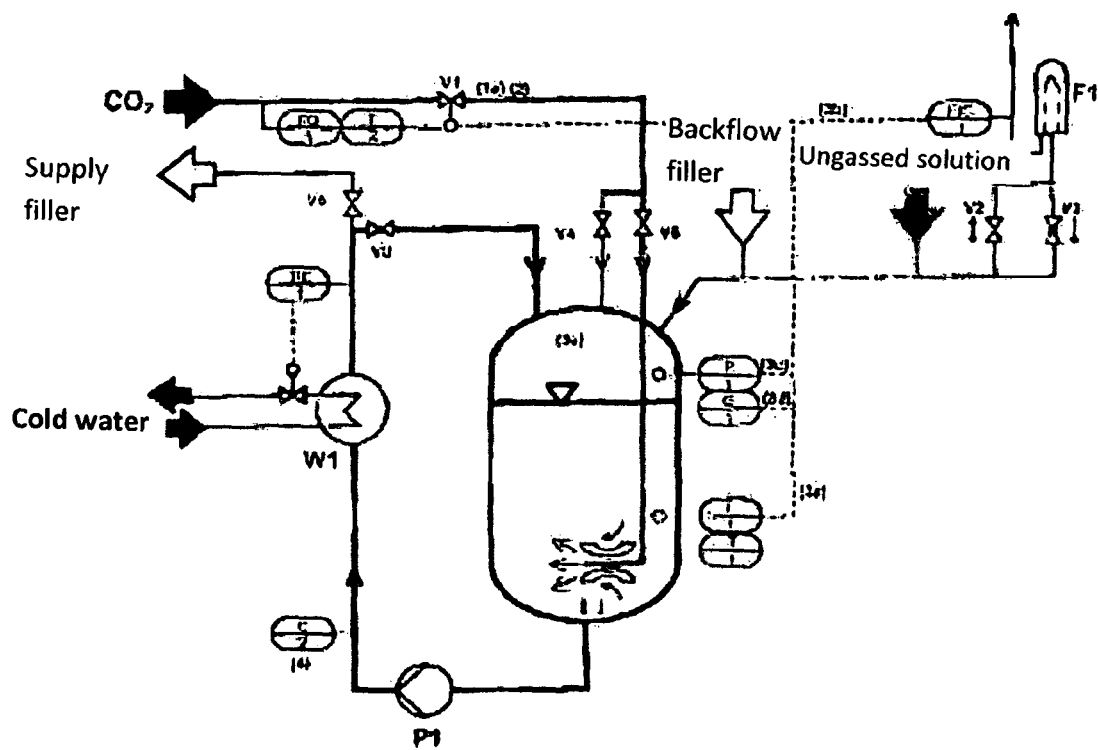
FIG. 1: a schematic diagram of the container of an embodiment of the apparatus in accordance with the invention.

Further scope of applicability of the present invention will become apparent from the detailed description given hereinafter. However, it should be understood that the detailed description and specific examples, while indicating preferred embodiments of the invention, are given by way of illustration only, since various changes and modification within the spirit and scope of the invention will become apparent to those skilled in the art from this detailed description.

In the embodiment of the present invention shown below, the method in accordance with the invention or the apparatus in accordance with the invention is used to keep the pH of a bicarbonate solution constant during the filling. In this connection, after the end of the preparation process of the bicarbonate solution, during which no measures at all are taken to set a specific pH, but during which rather the stripping of $CO_2$ is accepted, a quantity of $CO_2$ is first initially injected into the solution by nozzle which has previously been determined based on chemical-physical calculations. In the embodiment, for example in a batch container with 24,000 liters bicarbonate solution with 70 mmol/l bicarbonate, 10.5 kg $CO_2$, initially defined, is injected into the solution by nozzle in fine beads. In this connection, injector nozzles are used which permit the injection by nozzle in fine beads.

During the draining of the finished solution via a base opening of the batch container for the filling of the solution into plastic bags, for example, the pH of the solution must now be kept constant in accordance with the invention. For this purpose, an individually required refill gassing quantity of $CO_2$ for injection into the gas space by nozzle is calculated online in dependence on the filling level. It is taken into account in this connection that the physical marginal conditions are changed during the draining of the solution so that a shift in the chemical-physical equilibrium between the liquid and the gas space would occur without a refill gassing in accordance with the invention, which would result in a changed pH in the filled product.

During the emptying procedure (filling of the product, lowering of the filling level), the $CO_2$ quantity to be refilled is calculated in dependence on the filling level of the bicarbonate solution permanently measured by means of microwaves and just so much $CO_2$ is injected into the gas space by nozzle that the $CO_2$ quantity in the gas space corresponds to a calculated theoretical mean volume portion of 20.5% by volume $CO_2$. This amount determined on the basis of theoretical equilibrium calculation cannot, however, be measured at any point in the gas space because a gradient formation occurs in the gas space. A $CO_2$ measurement is not necessary at all in accordance with the invention, but it has rather surprisingly been found that the observation of these conditions ($x''_{CO2}$=20.5% by volume at 15° C. and 1 bar) on emptying also results in an observation of the pH of pH=7.2 in the bicarbonate solution with a previously unknown accuracy over longer time periods or over longer emptying procedures, e.g. several days.

Furthermore, ambient air flows over the sterile filter into the gas space to compensate the vacuum when the filling level is lowered. Interactions between the air or the $CO_2$ portion of the air and the bicarbonate solution have proven to be negligible in this connection. With closed reactors, the problem would result, in contrast, that the equilibrium conditions would change constantly in accordance with the changes in pressure. The method in accordance with the invention, in contrast, has the advantage that the pressure in the gas space can be kept constant by the flowing behind of air over the sterile filter and the $CO_2$ does not have to be added for pressure equalization, but rather the degree of freedom is present of adding $CO_2$ independently of the pressure equalization. It can also hereby be prevented in accordance with the invention that too much $CO_2$ is injected into the gas space by nozzle, which would result in an unwanted, pronounced lowering of the pH with the formation of steep gradients for $x'_{CO2}$ beneath the liquid level of the bicarbonate solution.

The embodiment of the present invention will now be explained in more detail again.

Product and Process Description

Specific solution types are gassed with carbon dioxide in accordance with their properties to be set within the framework of the manufacturing process for the purpose of manufacturing sterile medicine solutions or also medical product solutions. This is in particular done for the setting of a specific pH. In this connection, hydrogen carbonate (bicarbonate) or also other suitable raw substances are added to and dissolved in distilled water (WFI—water for injection).

In the given case, peritoneal dialysis solutions are manufactured in large-scale (up to 24,000 liters per batch) technical process plant and are filled in plastic bag systems with integrated tube and connector systems. In this connection, the solution is stored separately in the filled bag system as a dual-chamber solution until directly before use. The separated solution types in chamber 1 or chamber 2 of a bag system are termed the A solution or the B solution. In this connection, the so-called B solution represents the solution to be gassed with carbon dioxide.

The solutions are in each case prepared in correspondingly large containers (batch tanks B1) made of stainless steel, are chemically analyzed, are corrected under certain circumstances and are filter sterilized into a respectively downstream gas/liquid reactor (receiver B2 or B3). A batch line in each case comprises a batch tank and two receiver containers or gas/liquid reactors.

One of the batch lines, for example, serves the manufacture and provision of the B solution. Since the batch line has two sterile receiver containers B2 and B3, the batches are admittedly manufactured in batches, but can be filled quasi-continuously by changing or switching over the two receiver containers. The receiver container respectively not involved in the filling process is in the meantime in cleaning and sterilization phases. In the case of the bicarbonate B solution, the two receiver containers are in each case equivalent to a gas/liquid reactor due to the required gassing of the solution with carbon dioxide.

In the case of the B solution, the aforesaid gassing takes place in the state of the respective sterile receiver by means of carbon dioxide for the initial pH setting of the solution. Said gassing thus takes place after the preparation procedure of the chemical analysis and the sterile filtration into just these containers.

The gas is added during the process of the initial pH setting in each case via a distributor pipe attached in the base region of the containers. The supply by means of carbon dioxide takes place from a pressure gas bottle in pipe connection with the containers. The pressure gas bottle is installed in a decentral position in the production space.

After conclusion of the filtration process and of the initial setting of the pH, the solutions A and B are each run in circuit by means of ring conduits of approximately 100 m in length over the duration of the filling process. The two ring conduits lead from the receiver containers of the batch lines to the filler units of the spatially remotely disposed filling region.

A smaller part quantity is drawn off quasi-continuously via the respective fillers of the filling regions and a larger quantity is permanently returned into the respective tank via an immersion pipe.

The quantity drawn off in each case via a plurality of filling points of the filler units accordingly varies between a few 100 liters per hour to well above 1,000 liters per hour.

The part quantity drawn off in each case from the ring conduits by the filler units is conducted to the individual filling points via short stubs.

A discontinuous removal of the solution from the respective ring conduit of A and B solutions accordingly takes place.

To compensate the energy brought in via the pumps or the heating of the solution resulting therefrom, respective heat exchangers are connected after the pumps. The temperature can also be kept constant using these over a filling cycle from a receiver of several days.

The batch and receiver containers are released to the environment or into the production space via hydrophobic sterile filters.

The desired temperature range of the solution during filling is between 15° C. and 20° C. The filling of the dual chamber systems to be looked at in more detail here preferably takes place at a temperature of 15° C.

In the case of these solution types, the lower temperature is sensible due to the increased gas solubility of carbon dioxide at lower temperatures.

For reasons of the time procedure of the production sequence and due to the necessity of the sterilization of the receiver containers on each change of batch, a filtration of newly prepared solution quantities of around 15° C. into a very highly heated receiver container cannot be avoided. Accordingly, brief vacuums (collapsing of the residual vapor quantity) result due to such overlaps, but also temperature gradients of the sterile-filtered solution result if the change to the following batch has to be carried out directly after the completed filtration (and following filter integrity test). Only after a certain time can a temperature level of 15° C. be reached with the integrated heat exchangers already mentioned above in such cases.

The composition is reproduced in the following for the B solution of the so-called dual chamber solution to be considered here. Only sodium hydrogen carbonate is set as the charge substance in the solution type considered here.

Carbon dioxide is declared as an auxiliary substance for the pH setting. The quantity to be used will be described later.

TABLE 1-1

Declaration of the B solution
Declaration

| Cations | Anions |
|---|---|
| Sodium 70.00 mmol/l | Hydrogen carbonate 70.00 mmol/l |

TABLE 1-2

Constituents of the B solution
Constituents according to the declaration

| Raw material | Weighed portion/l |
|---|---|
| Water for injection purposes | 996.6 g |
| Sodium hydrogen carbonate Ph. Eur. | 5.881 g |

Carbon dioxide corresponding to a pH 7.2-7.3

In the case of the pH to be ensured here, a range of 7.2 to 7.3 pH units is to be ensured.

FIG. 1 shows as a schematic diagram the major technical plant relationships with respect to the absorption process of carbon dioxide in sterile medicine solutions.

Annotations to FIG. 1:
Designations
CIP Cleaning in place; distilled water 80° C., water for injection
SIP Sterilization in place; pure vapor 121° C.
$CO_2$ carbon dioxide
Apparatus and Instruments
I1, I2, I3 Injectors I1, I2, I3
BX Reactor B2 or B3 as sterile receiver with injectors I1, I2, I3

P1 Pump P1
W1 Heat exchanger W1
F1 Air filter F1 (hydrophobic sterile filter PVDF)
V1 Valve V1, main carbon dioxide supply
V2 Valve V2, release of the container to the environment
V3 Valve V3, check valve for container aeration
V4 Valve V4, carbon dioxide refilling in the gas space
V5 Valve V5, $CO_2$ supply in liquid
V6 Valve V6, supply filling
V7 Valve V7, bypass valve post dissolving of carbon dioxide
V8 Valve V8, "small" tank circuit"
Measuring Technology
FQ1/T2 Mass flow measurement $CO_2$
FIC1 Flow measurement of room air flowing behind
TIC1 Temperature control via cold water flow
Q1 Quality variable—$CO_2$-content of the vapor phase over the liquid surface
Q2 Quality variable—pH, inline measurement
P1 Pressure/partial pressure $CO_2$
L1 Filling level, container
T1 Temperature of the liquid
I1 Injector 1, gassing of the solution to set the pH
I2 Injector 2, post-dissolving of any superfluous carbon dioxide of the gas space
I3 Injector 3, mixing the bypass flow with "pre-dissolved" carbon dioxide from nozzle I2

Gassing Process of the Solution Before Filling

In the so-called B solution, bicarbonate (sodium hydrogen carbonate) is in an approximately thermodynamic equilibrium after the preparation with the carbon dioxide arising through chemical reaction. A pH of approximately 8.3 results in accordance with the measurements during the preparation procedure in the batch tank.

The solution is sterile-filtered into one of the two reactors B2 and B3 and is additionally gassed with carbon dioxide in them to set the pH.

The gassing preferably takes place via injector nozzles.

Setting the Final State of the Gassing

The gassing process took place arbitrarily in accordance with the experience values of the respective operator in known methods with respect to the reduced pressure of the pressure gas bottle to be adopted and the gassing period between the individual control measurements, with the process being overlaid by any simultaneous cooling down of the solution. The total process is only detected very subjectively in this context.

It was only possible to assume a representative pH status and to continue or, under certain circumstances, to terminate the gassing procedure after a plurality of gassing interruptions and respective pH measurements with unchanged values. A correspondingly larger time requirement resulted from this.

However, the accuracy of the pH measurements—even under ideal conditions and with a corresponding calibration—is also in turn generally only at around +/−0.05 pH units. The pH to be ensured over the total time period must be between 7.2 and 7.3 pH units. Since it can be found that the pH drifts toward higher values over the course of the filling time, the target value to be adopted is the lowest admissible value of 7.2 pH units.

The pH is ultimately unsuitable as a control variable for the carbon dioxide addition due to these relationships.

The approximation to the final state to be adopted during the gassing procedure accordingly did not take place in a manner leading to the desired result in known methods. The process could only be carried out iteratively.

Figure 2:
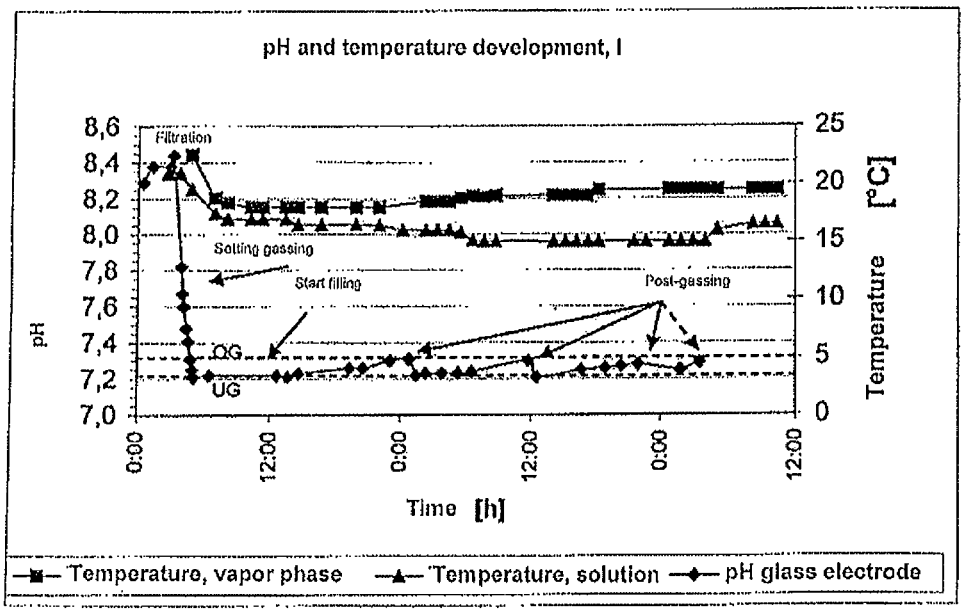
FIG. 2: the plot of the pH during the draining while using a method of the prior art.

In accordance with the present invention, in contrast, a reproducible adoption of the pH results before the filling with respect to the carbon dioxide gassing while taking account of the thermodynamic equilibrium state and the absorption behavior in the system $CO_2$—$NaHCO_3$—$H_2O$, (2) in FIG. 2-1

The valve V2 is closed over the period of the gassing so that no carbon dioxide can be output into the environment. The possibility is given of setting up a $CO_2$ equilibrium. In this connection, only the carbon dioxide added in the sterile reactor is understood with respect to the equilibrium, i.e. without the carbon dioxide already produced by reaction by the addition of bicarbonate during the preparation procedure. Any required inflow of ambient air over the sterile filter is in turn ensured via the check valve V3. The possible generation of a vacuum due to cooling can thus also be countered (high temperature of the container after sterilization).

A discharge of carbon dioxide is thus prevented.

The quality of the approximation to the phase equilibrium state of the system has to be determined for the relevant temperature and pressure ranges of the solution to be prepared. The thermodynamic equilibrium conditions state that the temperature, pressure and the chemical potentials are the same in all phases.

The carbon dioxide quantity additionally to be absorbed has to be determined for the pH to be adopted. The associated values of the carbon dioxide concentration in the gas and liquid phases and of the partial pressure of carbon dioxide of the gaseous phase also result for the sought pressure and temperature range in accordance with the equilibrium conditions.

Both the results of phase equilibrium calculations and measurements of the solution with respect to pH, pressure, temperature, concentration, $CO_2$ consumption and TIC (total inorganic carbon) serve to determine the corresponding data and ultimately to coordinate the production process with the theoretical data.

To detect the thermodynamic state of the system in the production process, it is expedient to determine the following values:

The temperature in the liquid and vapor phases, the total pressure or partial pressure of $CO_2$ in the top region of the reactor, the carbon dioxide portion in the vapor and liquid phases. The determination of the partial pressure changes of $CO_2$ can be realized by determining the total pressure at different times since a discharge of $CO_2$ is suppressed and any pressure increase during gassing is therefore only caused by $CO_2$.

Depending on the batch job, the carbon dioxide quantity to be added can likewise be determined with references to the recipe and to the solution quantity by means of the process guidance system in this case and the supply can be limited or stopped via a mass flow determination of carbon dioxide.

Measurements of the aforesaid process sizes then provide a statement on the quality of the approximation to the equilibrium state. An iterative procedure with numerous, time-consuming pH measurements is superfluous.

Carbon dioxide requirement calculated approximately.

An approximate calculation of the carbon dioxide requirement should be carried out here with reference to the law of mass action using literature values for the dissociation constant $K_s$, or the $pK_s$ value, to obtain a comparison or an estimate of results in this regard with respect to the real case.

The following apply to the reaction equations:

$$H_2O + CO_2 \rightleftharpoons H_2CO_3$$

$$H_2CO_3 \rightleftharpoons HCO_3^- + H^+$$

$$H_2O + CO_2 \rightleftharpoons HCO_3^- + H^+$$

The formation of $CO_3^{2-}$ (carbonate ion) can be neglected in the pH range considered.

The following applies to the equilibrium state in accordance with the above statements:

$$K_C = \frac{C_C^{vC} \cdot (C_D)^{vD}}{(C_A)^{|v_A|}(C_B)^{|v_B|}} \quad \frac{[(HCO)_3] \cdot [H^+]}{[H_2O] \cdot [CO_2]}$$

with $K_c$ as the equilibrium constant.

It can be assumed in a simplified manner due to the high excess of water:

$$K_C = \frac{[HCO_3^-] \cdot [H^+]}{[CO_2]} \text{ with } [HCO_3^-] = 70 \text{ mmol}/l = 0,07 \text{ mol}/l \text{ given from the "parent recipe" or the manufacturer's instructions}$$

According to Holleman and Wiberg, the conversion of carbon dioxide with water to carbonic acid $H_2CO_3$ only amounts to approximately 0.2%, however.

This carbonic acid, which cannot be isolated as a free acid, is theoretically a medium-strong acid with a dissociation constant $K_S$. In all formulae, $H^+$ stands for the actually present hydronium ion $H_3O^+$.

$$K_S = \frac{[HCO_3^-] \cdot [H^+]}{[H_2CO_3]} \quad 3 \times 10^{-4} \text{ or } pK_S = 3.88$$

Since, however, approx. 99.8% of the dissolved carbon dioxide is not present as $H_2CO_3$, but as hydrated $CO_2$, the total solution has the effect of a weak acid.

If now the undissociated acid portion is taken into account, a so-called "apparent dissociation constant" can be given and the actual character of the solution can thus more easily be described:

$$K_S = \frac{[HCO_3^-] \cdot [H^+]}{[H_2CO_3 + CO_2]} = 4,5 \times 10^{-7} \text{ or } pK_S = 6.35$$

with it still applying:
$pK_S = -\lg K_S$
$pK_S = 6.35$ [according to Hollemann and Wiberg]
$K_S = 10^{-6.35}$ The pH of the ungassed solution in the reactor (after filtration) in accordance with the measurements of the trial series amounts to approximately 8.5 pH units; the pH of the finally adopted solution after gassing 7.2.

Accordingly, it can be given for the proton concentration after definition of the pH:
ungassed: $[H^+] = 10^{-8.5}$ mol/l
gassed: $[H^+] = 10^{-7.2}$ mol/l It now results from the above relationship for the carbon dioxide concentration:

$$[CO_2] = \frac{[HCO_3^-] \cdot [H^+]}{K_S}$$

and with the above value for $pK_S = 6.35$, it follows:

$$\text{ungassed: } [CO_2] = \frac{0.07 \text{ mol}/l \cdot 10^{-8.5} \text{ mol}/l}{10^{-6.35} \text{ mol}/l} \cdot 10^{-3} \text{ mol}/l$$

$$\text{gassed: } [CO_2] = \frac{0.07 \text{ mol}/l \cdot 10^{-7.2} \text{ mol}/l}{10^{-6.35} \text{ mol}/l} \cdot 10^{-3} \text{ mol}/l$$

Accordingly, there results as the difference between the start and the end of the gassing for the change in the carbon dioxide concentration:

$[CO_2]_{end} - [CO_2]_{start} = 0.008321$ mol/l

With a molecular weight for carbon dioxide of 44.011 g/mol [Messrs. Linde Gas], a carbon dioxide requirement for 1 liter solution thus results:

$m_{CO2} = M_{CO2} \cdot [CO2] = 44.011$ g/mol·0.008321 mol/l=0.366216 g/l or: 8.789 kg carbon dioxide/24,000 liters The above calculation only takes account of the 24 m³ solution quantity with respect to the calculation of the volume, but the given reactor has a content of 26.8 m³. It can be seen from the theoretical calculations on the phase equilibrium (see Annex B) that the vapor phase has approximately 1.054 kg carbon dioxide with a solution quantity of 24 m³. To be able to generally compare the results with one another, the above result is corrected by this value and, after the addition of both values, a carbon dioxide requirement for 24,000 liters of solution in the reactor is obtained of:

$m1 + m2 = m_{tot}$ 8.789 kg + 1.054 kg = 9.843 kg carbon dioxide/24,000 liters of solution in the reactor In the idealized calculation by means of the law of mass effect, in particular the present of sodium hydrogen carbonate is not taken into account, nor the carbon dioxide quantity resulting herefrom.

Comparison measurements were therefore taken into account with respect to the $CO_2$ quantity actually required to set the pH.

The quantity of carbon dioxide to be added to be able to set the solution purposefully is determined.

There is thus the possibility in accordance with the specific carbon dioxide quantities for the container to have the corresponding carbon dioxide quantity to be metered calculated automatically with respect to the individual filling levels by means of the process guidance system—using the respectively preselected solution quantity—and to stop the gas supply in an automated manner when the metered target value of the carbon dioxide is reached. The factors of different filling levels is thus also taken into account. A subsequent pH determination can then confirm the pH of 7.2 to be reached.

Observed in absolute quantities, a somewhat lower requirement results in the case of higher solution quantities.

If the observation is simplified without distinguishing the type of gassing and the solution quantities, the absolute range of carbon dioxide quantities used extends from 10.25 kg to 12.9 kg.

This can then be compared with the results of the theoretical calculations on the phase equilibrium.

A specific carbon dioxide quantity is required in the liquid and in the vapor phase. If the filling level falls, carbon dioxide moves from the liquid into the vapor phase. The portion of carbon dioxide in the liquid phase or the vapor phase varies in dependence on the filling level.

The calculations for the equilibrium state for the present system produce a mean value of approx. 10.5 kg carbon dioxide.

Viewed in total, a good approximation to this theoretical state, which can only be reached approximately for real relationships, can thus be found with the above values.

Evaluations of experiments have shown that the gassing time can admittedly vary over the trial series, but the carbon dioxide quantity to be used is very largely not influenced by this.

Savings result in this connection due to the direct predetermination of a carbon dioxide quantity to be metered with respect to low staff requirements and to an increased plant availability of the production of the batch line. Starting from a three-time stopping of the gassing mode and a corresponding sample taking, the calibration of the pH measurement in the lab, the counter-measurement and the repeated start of the gassing, a pH determination is now only required once after the reaching of the purposefully started end state to confirm the state reached.

With a time requirement for each above-described action of around 20 minutes, a saving in personnel requirements of around 40 minutes per batch results. Equally, an increased plant availability, availability of the lab instruments and a saving of consumables.

Drift of the pH over the time period of the filling in the method in accordance with the prior art:

The filling of the solution causes a constant reduction in the filling level of the sterile reactor over a period of approx. forty hours. It is to be found over this process period that the pH of the solution increases successively in known methods and exceeds an upper limit value of pH 7.3.

In this state, the filling is usually interrupted by an automated closing of the filling valves due to the installed inline pH probe.

The solution is not post-gassed with carbon dioxide for some minutes based on experience values of the respective operator.

The gassing is terminated after a certain time and the pH achieved is determined a plurality of times by means of the sample and the lab pH meter. This procedure is repeated correspondingly frequently until the reaching of a pH between 7.2 and 7.3. In this connection—in accordance with the original setting after the preparation of the solution—an adjustment to the lower limit value 7.2 is again desired since an increase in the pH continues to take place as the filling level falls.

The installed inline probe is optionally matched to the current value via its measuring transducer with reference to the pH measurement by means of the lab pH meter The production downtime, or the standstill of such a post-gassing action, amounts in each case to approximately 45 minutes. The time development of the occurrence is equally dependent on the quality of the original starting setting and experience has shown that it can be necessary approximately four times within the framework of a filling cycle of a batch—even with an ideal setting of the solution close to the lower limit pH 7.2.

FIG. 2 shows the status quo or the use of the previous gassing and filling process with respect to the pH development.

The present invention in contrast makes possible a stabilization of the pH during the filling by resupplying of carbon dioxide in accordance with the state variables in the thermodynamic equilibrium in dependence on the filling level of the container.

The arising additional volume is replaced by room air flowing behind over the sterile air filter during the filling process. The carbon dioxide concentration in the gas space of the reactor thereby falls with respect to the initial situation.

An equilibrium state is thus continuously adopted again approximately between the two phases. This results in the discharge of carbon dioxide from the solution into the vapor phase, whereby the pH of the solution increases and also moves above the upper limit of 7.3 pH units after a certain time.

The check valve V3 permits a flowing behind of room air during the filling process or on a falling reactor filling level whereby the forming of a vacuum is prevented. Equally, small quantities of carbon dioxide are added quasi-continuously separately into the gas space via the valve V2—in dependence on the measured filling level and the known carbon dioxide concentration of the vapor phase in the phase equilibrium. The outflow of any gas portions is prevented due to the check valve and the air filter valve V2 which is closed during the filling period.

The permanent backflow of the solution quantity run in the filling circuit or "big circuit" takes place via an immersion pipe so that a direct absorption of carbon dioxide is avoided on any passing of the liquid jet through the vapor phase.

The thermodynamic state between the vapor phase and the liquid phase or the initially adopted approximate equilibrium state in the reactor is almost maintained and a desorption of carbon dioxide or an increase in the pH is countered.

In summary, it can be stated that the creation of a gradient of the pH over the filling period of the respective batch (approx. 24,000 bag systems) is suppressed by this procedure since no drift of the pH occurs.

Since around four post-gassing actions thereby become superfluous per filled batch, a production downtime of around 3 hours per batch can be avoided.

Alternative solution concept: stabilization of the pH during the filling by resupplying carbon dioxide in accordance with the state variables in thermodynamic equilibrium in dependence on the quantity of room air flowing behind.

Based on the procedure just shown, it is conceivable only to carry out the resupply of carbon dioxide by means of SPS control when an inflow or sucking in of room air is equally given over the sterile filter—due to the fall in the filling level and the arising vacuum—(V2 permanently open). To determine this state, a corresponding flow measurement operative in the fine range must be provided in the region of the filter (FIC1), said flow measurement controlling the supply of carbon dioxide via the valve V1.

The addition of $CO_2$ should take place in accordance with the mol portion in the equilibrium state to be determined theoretically. The mol portion must remain the same over the filling period since actually the pH, the temperature, the pressure, the composition of the solution system should also be maintained. The carbon dioxide supply would only be determined beyond this by the quantity of the inflowing room air and accordingly by the filling speed of the filler units or bag systems.

When the gas supply valve V1 is designed as a control valve, the quantity of the inflowing room air can therefore equally deliver the desired set value for the gas supply valve V1 in order thus to maintain the predetermined ratio of carbon dioxide to room air in the vapor phase of the container. The system thus reacts directly to filling procedures of different speed. The supply of carbon dioxide takes place continuously, in contrast to the statements on the above case, precisely over the period in which a supply of room air is also given. The setting of the composition of the vapor phase of the reactor thereby takes place purposefully and directly results in stable conditions.

The solution of the resupply of carbon dioxide in accordance with the room air quantity flowing behind into the plant is, however, problematic since the gas tightness of the reactor system must be given with respect to the connected pipe conduits. A control based on the change in the filling level is therefore to be preferred.

The resupplied quantity is supplied to the system in a controlled manner in accordance with the speed of the filling level fall and takes account of the composition in the theoretically determined phase equilibrium state, in the solution system observed here with around 20.5% by volume carbon dioxide in the vapor phase.

The good reproducibility of the resupplied carbon dioxide quantity to the amount of 11.15 kg (FIG. 3) over the setting consumption of 12.9 kg and over the carbon dioxide quantity determined on the basis of theoretical calculations in the case of the phase equilibrium for the case of the just emptied reactor (10.09) kg is interesting. If an ideally developing constant pH and the maintenance of a phase equilibrium state are assumed, the portion of the carbon dioxide quantity already in the reactor in the vapor phase at 24,000 liters content would still have to be added. According to the values calculated, this quantity would correspond to around 1.05 kg carbon dioxide. A negligible amount would be added due to the carbon dioxide present in the sucked in room air.

Since the control is based on the fall in the filling level measured in the reactor, the reactor reacts to changes in the spatially very remote production line of the filling automatically in this sense with the above control and without any further manual support.

The control structure is also described in more detail in the further statements. In the following, the result should be reproduced again with reference to the curve representations of the pH measurement without any further explanations.

The method prepared here is called the so-called "headspace method" in this connection.

Figure 3:
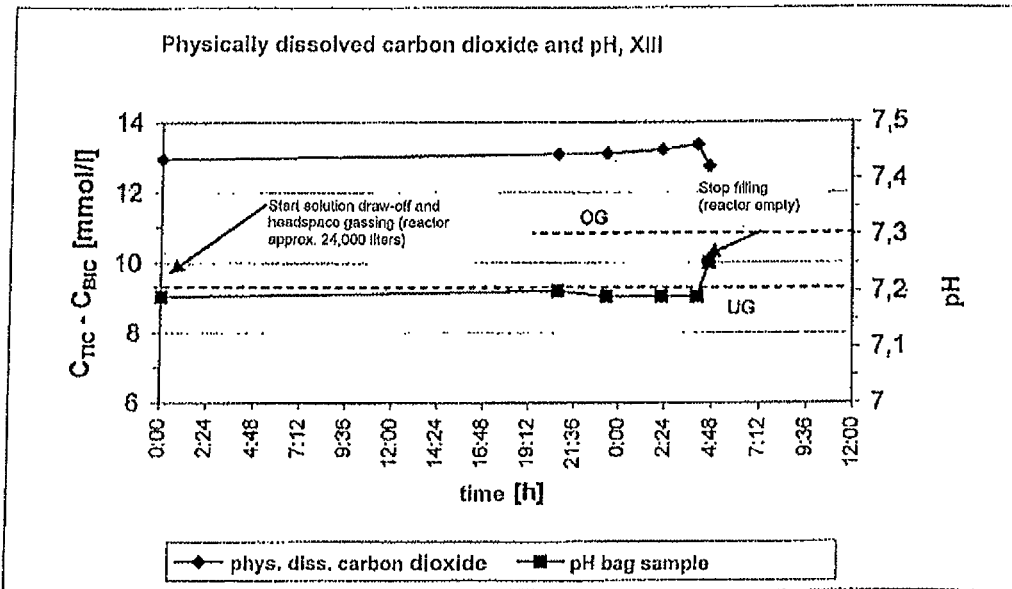
FIG. 3: the plot of the pH during the draining while using an embodiment of the method in accordance with the invention.

The representation in FIG. 3 shows a pH development remaining constant up to directly before the end of the filling (in contrast to the evaluation in accordance with FIG. 2).

It must be pointed out at this point that an increase in the permitted pH limit also does not protect against the required past-gassing actions. The curve development (see FIG. 2) of the pH reproduced in the framework of trial series I illustrates the fast increase to higher values; the gradient of the curve shows that, for example, an increase in the permitted IPK upper limit to pH 7.4 cannot represent a solution to the problem.

Improvement possibilities due to a corresponding design of the immersion pipe (arrangement in the vicinity of the container outflow) results in the case of the reactor running empty. An increase in pH is briefly given there due to the exit of the immersed backflow conduit from the liquid surface (see FIG. 3). Up to now, this state is never reached due to the production process of the filling line since the residual quantity of a few liters is thrown away before the running empty of the reactor and the reactor is emptied by means of a separate control.

Since, however, the running empty of the reactor would be associated with an automatic switching over from one reactor to the other, a desired semi-continuous operation could thus be realized. Even with a given increase in the pH, it is still in the permitted range, i.e. smaller than 7.3 pH units. This is ultimately made possible by the preceding keeping constant of the pH at pH=7.2.

A reduction in the personnel effort results with the realization of this method due to the omission of post-gassing actions of around 45 minutes per interruption with around 2 to 4 interruptions depending on the solution quantity or on the filling period over the time of the filling. Depending on the order situation or on the market demand for different bag sizes of a solution type, an annually calculable solution quantity to be filled results. The demand of distribution from different countries controls the bag numbers required at specific times and thus predetermines the batch sizes or reactor filling quantities.

In contrast to the two to four interruptions of production of around 45 minutes each shown above, the previous substantial production downtimes are avoided with the application of the method in accordance with the invention in the solution type observed. Furthermore, the personnel effort for the carrying out of post-gassing actions is minimized accordingly.

The increased effort arising due to the installation of a control valve, of the associated piping and a flow quantity measurement for carbon dioxide plus the increased demands for carbon dioxide (11.15 kg, FIG. 3) is marginal compared with the saving.

Figure 4:
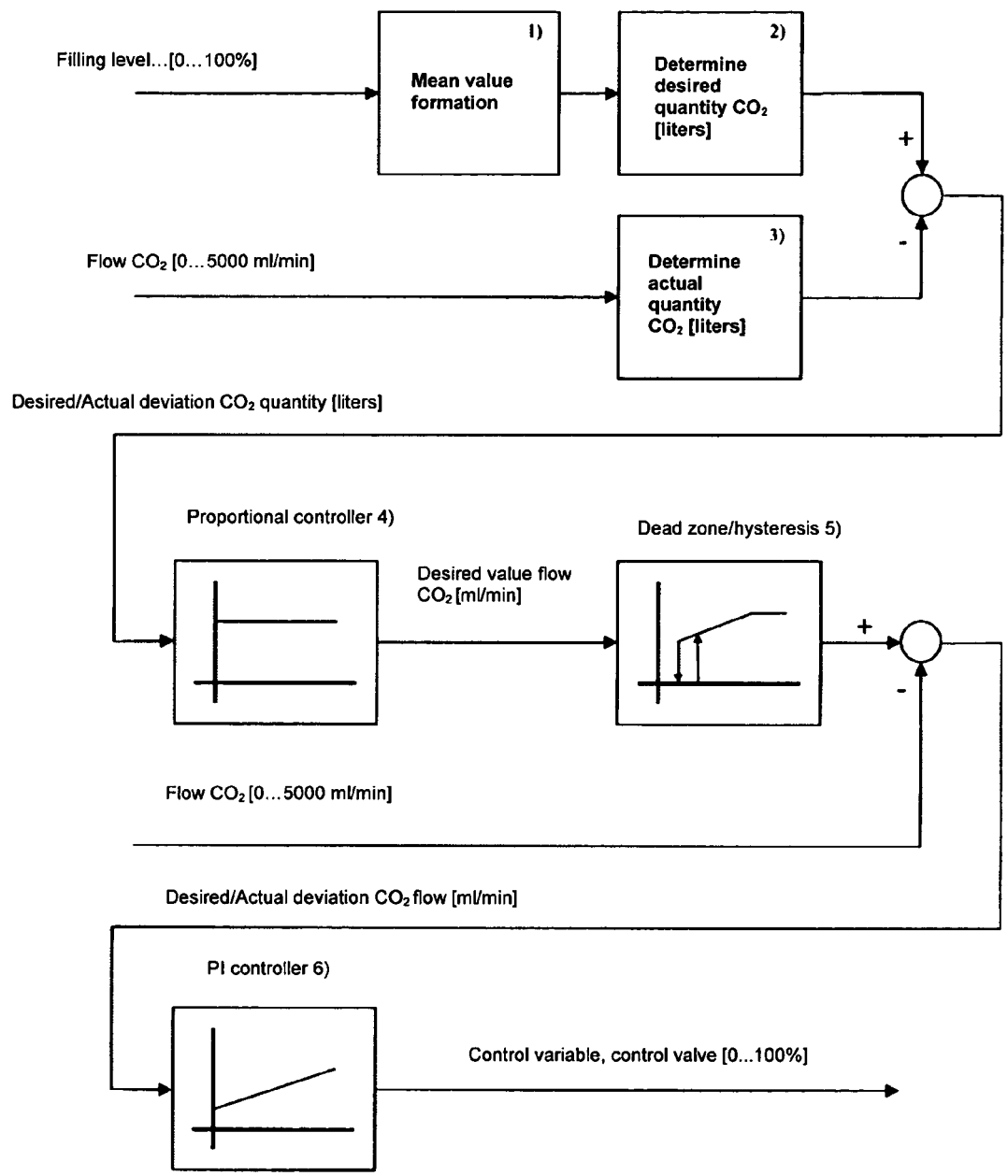
FIG. 4 a flow diagram of an embodiment of the control in accordance with the invention.

FIG. 4 shows the schematic control procedure starting from the input signal (filling level 0% to 100%) up to the control variable (0% to 100%) of the control valve.

The implementation took place on a memory-programmable control S5-115 U CPU 944 B.

The numbers 1) to 6) shown in the control scheme in FIG. 4 will be briefly explained in the following:

1) Mean value formation from 100 values (one new value a second).
2) 1% filling level fall corresponds to 250 liters filled solution, or 250 liters volume increase.
   20.5% (carbon dioxide; from phase equilibrium observations) of 250 liters, 51.25 liters of carbon dioxide to be added per 1% filling level fall results.
3) Actual amount by integration of the flow over time.
4) proportional controller for evaluation of the desired/actual comparison of the carbon dioxide quantity, or as an amplification factor, to achieve a control behavior which is as stable as possible (starting value corresponds to the desired flow of carbon dioxide).
   Amplification factor=100, i.e. the desired value for the flow is increased by 100 ml/min per liter desired/actual deviation of the CO2 quantity.
5) taking account of a dead zone/hysteresis to remain within a sensible or permitted working range from 1 to 5 l/min of carbon dioxide to be measured.
   Desired value CO2 flow is set to 0 ml/min with an increase up to 1000 ml, with a fall from 900 ml/min (prevention of "creep flows" or, if, for example, fewer than 10 liters CO2 are missing, the control valve would remain closed (10 liters input value×amplification=1000 ml/min starting value).
   From 5,000 ml/min, the desired value is set to or "frozen" at 5,000 ml/min (maximum measurement range of the flow meter).
6) PI controller of the control valve to "stabilize" or approximate the desired/actual state. To achieve a control behavior which is as stable as possible, a desired/actual deviation is evaluated at 5%.

The present invention thus shows a method which ensures a previously set system state of the liquid phase with respect to a pH to be kept constant by resupplying carbon dioxide into the vapor phase of gas/liquid reactors. The method is called a "headspace method" in this connection. In this context, the maintenance of an approximated phase equilibrium state prevents the stripping of carbon dioxide from the given liquid phase.

By implementation of the "headspace method", the personnel effort can be reduced and in particular the plant availability of the respective production line can be increased.

Equally, the present invention can advantageously be used in the manufacture or filling of further solutions, e.g. in a solution to be gassed with carbon dioxide with changed hydrogen carbonate content and added sodium chloride as electrolytes.

In accordance with the determined theoretical carbon dioxide concentrations of the thermodynamic equilibrium, a solution adjustment is made analogously for this solution system and carbon dioxide is resupplied into the reactor head.

The headspace method in accordance with the invention can equally advantageously be used in further medical product solutions or medicine solutions which have to be gassed with carbon dioxide.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method for keeping constant a pH of a medical liquid being drained from a container, said method comprising:
providing $CO_2$ and at least one other gas or gas mixture to the container during the draining of the medical liquid, with a quantity of the $CO_2$ that is to be provided being determined from a step of measuring a change in a level of the medical liquid in the container.

2. The method in accordance with claim 1, further comprising a step of determining a change in a gas space volume over the medical liquid in the container based on the change in the level of the liquid, and determining a quantity of the $CO_2$ to be added based on the step of determining the change in the gas space volume.

3. The method in accordance with claim 1, further comprising a step of flowing ambient air through a sterile filter so that, on a change in the level of the medical liquid, a pressure in a gas space is automatically approximated to that of ambient pressure.

4. The method in accordance with claim 1, wherein the $CO_2$ is added in such a quantity that a mean $CO_2$ volume portion in a gas space as determined by calculation remains constant.

5. The method in accordance with claim 1, wherein a quantity of the $CO_2$ to be added is determined based on a chemical-physical equilibrium determined by calculation between the medical liquid and a gas space disposed above it.

6. The method in accordance with claim 1, wherein a determination of a quantity of the $CO_2$ to be added is made without a measurement of the pH of the medical liquid.

7. The method in accordance with claim 1, wherein a determination of a quantity of the $CO_2$ to be added is made without a measurement of a $CO_2$ concentration in a gas space.

8. The method in accordance with claim 1, wherein the $CO_2$ and the at least one other gas or gas mixture flow into a gas space above a level of the medical liquid during the draining of the medical liquid.

9. The method in accordance with claim 1, further comprising a step of injecting a previously determined quantity of the $CO_2$ into the medical liquid by nozzle before the draining of the medical liquid.

10. The method in accordance with claim 1, wherein the medical liquid is a bicarbonate solution.

11. An apparatus for keeping constant a pH of a medical liquid being drained from a container having an outlet for the medical liquid, at least one inlet for $CO_2$, and an inlet for at least one other gas or gas mixture, said apparatus comprising:
an element for measuring a change in a level of the medical liquid in the container; and
an electronic control for determining and automatically supplying a $CO_2$ quantity during the draining of the medical liquid,
with the $CO_2$ quantity that is to be supplied being determined from the measured change in the level of the medical liquid in the container.

12. The apparatus in accordance with claim 11, wherein the element for measuring the change in the level of the medical liquid in the container is a transducer.

13. The apparatus in accordance with claim 11, further comprising a connection between a gas space of the container and an environment by which ambient air can flow into the gas space through a sterile filter.

14. The apparatus according to claim 12, wherein the transducer determines the level of the medical liquid via microwave measurement or radar measurement.

* * * * *

UNITED STATES PATENT AND TRADEMARK OFFICE
CERTIFICATE OF CORRECTION

PATENT NO. : 8,486,272 B2  
APPLICATION NO. : 12/733116  
DATED : July 16, 2013  
INVENTOR(S) : Rauch Page 1 of 1

It is certified that error appears in the above-identified patent and that said Letters Patent is hereby corrected as shown below:

On the Title page of the patent, column 1, Item (75), change "Langweller" to -- Langweiler --.

In the Claims

Column 11, line 6, change "$C_c$" to -- $(C_c)$ --; and change "$(HC0)_3$" to -- $HC0_3^-$ --;

line 47, change "Ig" to -- lg --;

line 58, change "72" to -- 7.2 --.

Signed and Sealed this  
Twenty-eighth Day of January, 2014

Michelle K. Lee  
*Deputy Director of the United States Patent and Trademark Office*

UNITED STATES PATENT AND TRADEMARK OFFICE
CERTIFICATE OF CORRECTION

PATENT NO.       : 8,486,272 B2                                   Page 1 of 1
APPLICATION NO. : 12/733116
DATED            : July 16, 2013
INVENTOR(S)      : Achim Rauch It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 476 days.

Signed and Sealed this
Eighth Day of September, 2015

Michelle K. Lee
*Director of the United States Patent and Trademark Office*